(12) United States Patent
Huth et al.

(10) Patent No.: US 7,202,260 B2
(45) Date of Patent: Apr. 10, 2007

(54) VEGFR-2 AND VEGFR-3 INHIBITORY ANTHRANILAMIDE PYRIDONES

(75) Inventors: Andreas Huth, Berlin (DE); Martin Krueger, Berlin (DE); Ludwig Zorn, Berlin (DE); Stuart Ince, Berlin (DE); Rolf Bohlmann, Berlin (DE); Karl Heinz Thierauch, Berlin (DE); Andreas Menrad, Oranienburg (DE); Martin Haberey, Berlin (DE); Holger Hess-Stumpp, Berlin (DE)

(73) Assignee: Schering AG, Darmstadt (DE)

( * ) Notice: Subject to any disclaimer, the term of this patent is extended or adjusted under 35 U.S.C. 154(b) by 96 days.

(21) Appl. No.: 10/866,078

(22) Filed: Jun. 14, 2004

(65) Prior Publication Data

US 2005/0049281 A1  Mar. 3, 2005

Related U.S. Application Data

(60) Provisional application No. 60/482,009, filed on Jun. 25, 2003.

(30) Foreign Application Priority Data

Jun. 13, 2003  (DE) ................. 103 27 719

(51) Int. Cl.
   *C07D 401/01*  (2006.01)
   *C07D 213/02*  (2006.01)
   *A61K 31/44*  (2006.01)

(52) U.S. Cl. ............ 514/332; 514/351; 546/255; 546/300

(58) Field of Classification Search ........... 514/332, 514/351; 546/255, 300
   See application file for complete search history.

(56) References Cited

U.S. PATENT DOCUMENTS

| | | |
|---|---|---|
| 6,548,548 B2 | 4/2003 | Campbell et al. |
| 2004/0039019 A1 | 2/2004 | Huth et al. |
| 2004/0102441 A1 | 5/2004 | Krueger et al. |

FOREIGN PATENT DOCUMENTS

| | | |
|---|---|---|
| DE | 10023486 | 3/2002 |
| DE | 10228090 | 1/2004 |
| WO | WO 0027819 | 5/2000 |
| WO | WO 0027820 | 5/2000 |
| WO | WO 02090352 | 11/2002 |
| WO | WO 03040102 | 5/2003 |

*Primary Examiner*—Zinna N. Davis
(74) *Attorney, Agent, or Firm*—Millen, White, Zelano & Branigan, P.C.

(57) ABSTRACT

Novel VEGFR-2 and VEGFR-3 inhibitory anthranilamide pyridones and their use as pharmaceutical agents for treating diseases that are triggered by persistent angiogenesis are selected.

14 Claims, No Drawings

VEGFR-2 AND VEGFR-3 INHIBITORY ANTHRANILAMIDE PYRIDONES

This application claims the benefit of the filing date of U.S. Provisional Application Ser. No. 60/482,009 filed Jun. 25, 2003.

The invention relates to VEGFR-2 and VEGFR-3 inhibitory anthranilamide pyridones and their use as pharmaceutical agents for treating diseases that are triggered by persistent angiogenesis.

Persistent angiogenesis can be the cause or precondition of various diseases, such as tumor or metastasis growth, psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases and arteriosclerosis, or can result in an aggravation of these diseases.

Persistent angiogenesis is induced by the factor VEGF via its receptor. So that VEGF can exert this action, it is necessary that VEGF bind to the receptor, and a tyrosine phosphorylation is induced.

Direct or indirect inhibition of the VEGF receptor (VEGF=vascular endothelial growth factor) can be used for treating such diseases and other VEGF-induced pathological angiogenesis and vascular permeable conditions, such as tumor vascularization. For example, it is known that the growth of tumors can be inhibited by soluble receptors and antibodies against VEGF.

Anthranilamide pyridonamides that are used as pharmaceutical agents for treating psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, are known from WO 00/27820 (e.g., Example 38).

The compounds that are known from WO 00/27820 are generally effective in the indications cited, but their effectiveness is not very pronounced.

Anthranilic acid amides that are highly effective but also exhibit good inhibition of the Cytochrome P 450 isoenzyme 3A4 are also known from WO 03/040102. The Cytochrome P 450 isoenzyme 3A4 is one of the essential metabolic enzymes via which pharmaceutical agents are degraded. An inhibition of this isoenzyme results in undesirable pharmaceutical agent interactions, especially in the case of multi-morbid patients (patients with multiple disease conditions). There also exists the problem that in a combination therapy with other medications, increased toxicity occurs, which results from the inhibition of the degradation of the compounds and the associated excessive serum levels.

There is therefore the desire for active ingredients that on the one hand are effective and on the other hand are more compatible or do not exhibit any undesirable side effects.

It has now been found that compounds of general formula I

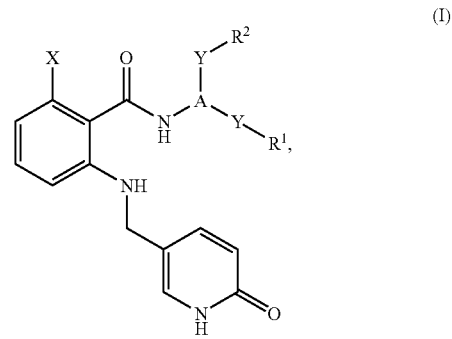

in which
A stands for an aryl or heteroaryl,
X stands for hydrogen or fluorine,
$R^1$ and $R^2$, independently of one another, stand for hydrogen, halogen, $C_1$–$C_{12}$-alkyl, $C_1$–$C_{12}$-alkoxy-$C_1$–$C_{10}$-alkylene, halo-$C_1$–$C_{10}$-alkyl, $C_3$–$C_{10}$-cycloalkyl or halo-$C_3$–$C_{10}$-cycloalkyl, and
Y stands for a bond or for oxygen or for the group —S—, —S(O)— or —SO$_2$—, as well as isomers, enantiomers, diastereomers and salts thereof, overcome the above-indicated drawbacks.

Alkyl is defined in each case as a straight-chain or branched alkyl radical, such as, for example, methyl, ethyl, propyl, isopropyl, butyl, isobutyl, sec-butyl, pentyl, isopentyl or hexyl, heptyl, octyl, nonyl, decyl, undecyl, or dodecyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy, decyloxy, undecyloxy or dodecyloxy.

Cycloalkyls are defined as monocyclic alkyl rings, such as cyclopropyl, cyclobutyl, cyclopentyl, cyclohexyl, or cycloheptyl, cyclooctyl, cyclononyl or cyclodecyl, but also bicyclic rings or tricyclic rings, such as, for example, adamantanyl.

Cycloalkyl radicals can contain, instead of the carbon atoms, one or more heteroatoms, such as oxygen, sulfur and/or nitrogen. Those heterocycloalkyls with 3 to 8 ring atoms are preferred.

Halogen is defined in each case as fluorine, chlorine, bromine or iodine.

Haloalkyl is defined as an alkyl radical, which can be substituted in one or more places with halogen.

The aryl radical in each case comprises 3–12 carbon atoms and can in each case be benzocondensed.

For example, there can be mentioned: cyclopropenyl, cyclopentadienyl, phenyl, tropyl, cyclooctadienyl, indenyl, naphthyl, azulenyl, biphenyl, fluorenyl, anthracenyl, etc.

The heteroaryl radical in each case comprises 3–16 ring atoms, and instead of the carbon can contain one or more heteroatoms that are the same or different, such as oxygen, nitrogen or sulfur, in the ring, and can be monocyclic, bicyclic, or tricyclic, and in addition in each case can be benzocondensed.

For example, there can be mentioned:
Thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyimidinyl, pyrazinyl, triazinyl, etc., and benzo derivatives thereof, such as, e.g., quinolyl, isoquinolyl, etc.; or azocinyl, indolizinyl, purinyl, etc., and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc.

If an acid group is included, the physiologically compatible salts of organic and inorganic bases are suitable as salts, such as, for example, the readily soluble alkali salts and alkaline-earth salts as well as N-methyl-glucamine, dimethyl-glucamine, ethyl-glucamine, lysine, 1,6-hexadiamine, ethanolamine, glucosamine, sarcosine, serinol, tris-hydroxymethyl-amino-methane, aminopropanediol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, fumaric acid, i.a.

Those compounds of general formula I in which
A stands for a phenyl or pyridyl,
X stands for hydrogen or fluorine,
$R^1$ and $R^2$, independently of one another, stand for hydrogen, halogen, $C_1$–$C_{12}$-alkyl, $C_1$–$C_{12}$-alkoxy-$C_1$–$C_{10}$-alkylene, halo-$C_1$–$C_{10}$-alkyl, $C_3$–$C_{10}$-cycloalkyl or halo-$C_3$–$C_{10}$-cycloalkyl and
Y stands for a bond or for oxygen or for the group —S—, —S(O)— or —SO$_2$—, as well as isomers, enantiomers, diastereomer and salts thereof, have special properties.

Those compounds of general formula I in which
A stands for a phenyl,
X stands for hydrogen or fluorine,
$R^1$ and $R^2$, independently of one another, stand for hydrogen, halogen, $C_1$–$C_{12}$-alkyl, $C_1$–$C_{12}$-alkoxy-$C_1$–$C_{10}$-alkylene, halo-$C_1$–$C_{10}$-alkyl, $C_3$–$C_{10}$-cycloalkyl or halo-$C_3$–$C_{10}$-cycloalkyl, and
Y stands for a bond or for oxygen or for the group —S—, —S(O)— or —SO$_2$—, as well as isomers, enantiomers, diastereomers, and salts thereof, are especially advantageous.

Those compounds of general formula I in which
A stands for a phenyl,
X stands for hydrogen,
$R^1$ and $R^2$, independently of one another, stand for hydrogen, halogen, $C_1$–$C_{12}$-alkyl, $C_1$–$C_{12}$-alkoxy-$C_1$–$C_{10}$-alkylene, halo-$C_1$–$C_{10}$-alkyl, $C_3$–$C_{10}$-cycloalkyl or halo-$C_3$–$C_{10}$-cycloalkyl, and
Y stands for a bond or for oxygen or for the group —S—, —S(O)— or —SO$_2$—, as well as isomers, enantiomers, diastereomers, and salts thereof, are preferred.

The compounds of general formula I according to the invention also contain the possible tautomeric forms and comprise the E- or Z-isomers or, if a chiral center is present, also the racemates and enantiomers.

The compounds of formula I as well as their physiologically compatible salts can be used as pharmaceutical agents based on their inhibitory activity relative to the phosphorylation of the VEGF receptor. Based on their profile of action, the compounds according to the invention are suitable for treating diseases that are caused or promoted by persistent angiogenesis.

Since the compounds of formula I are identified as inhibitors of the tyrosine kinases KDR, FLT-1 and FLT-4, they are suitable in particular for treating those diseases that are caused or promoted by persistent angiogenesis that is triggered via the VEGF receptor or by an increase in vascular permeability.

The subject of this invention is also the use of the compounds according to the invention as inhibitors of the tyrosine kinases KDR, FLT-1 and FLT-4.

Subjects of this invention are thus also pharmaceutical agents for treating tumors or use thereof.

The compounds according to the invention can be used either alone or in a formulation as pharmaceutical agents for treating tumor or metastasis growth, psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as immunosuppressive agents, for supporting scar-free healing, in senile keratosis and in contact dermatitis.

In treating injuries to nerve tissue, quick scar formation on the injury sites can be prevented with the compounds according to the invention, i.e., scar formation is prevented from occurring before the axons reconnect. A reconstruction of the nerve compounds would thus be facilitated.

The formation of ascites in patients can also be suppressed with the compounds according to the invention. VEGF-induced edemas can also be suppressed.

Lymphangiogenesis plays an important role in lymphogenic metastasizing (Karpanen, T. et al., Cancere Res. 2001 Mar. 1, 61(5): 1786–90, Veikkola, T., et al., EMBO J. 2001, Mar. 15; 20 (6): 1223–31).

The compounds according to the invention now also show excellent action as VEGFR kinase 3 inhibitors and are therefore also suitable as effective inhibitors of lymphangiogenesis.

By a treatment with the compounds according to the invention, not only a reduction of the size of metastases but also a reduction of the number of metastases is achieved.

Such pharmaceutical agents, their formulations and uses are also subjects of this invention.

The invention thus also relates to the use of the compounds of general formula I for the production of a pharmaceutical agent for use as or for treatment of psoriasis, Kaposi's sarcoma, restenosis, such as, e.g., stent-induced restenosis, endometriosis, Crohn's disease, Hodgkin's disease, leukemia; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, and for inhibiting the reocclusion of vessels after balloon catheter treatment, in vascular prosthetics or after mechanical devices are used to keep vessels open, such as, e.g., stents, as inmunosuppressive agents, as a support in scar-free healing, in senile keratosis and in contact dermatitis.

The formation of ascites in patients can also be suppressed with the compounds according to the invention. VEGF-induced edemas can also be suppressed.

To use the compounds of formula I as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions or emulsions. They optionally contain, moreover, adjuvants such as preservatives, stabilizers, wetting agents or emulsifiers, salts for changing osmotic pressure or buffers.

For parenteral administration, especially injection solutions or suspensions, especially aqueous solutions of the active compounds in polyhydroxyethoxylated castor oil, are suitable.

As carrier systems, surface-active adjuvants such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as for example, lactose, corn starch or potato starch, are suitable. The administration can also be carried out in liquid form, such as, for example, as juice, to which optionally a sweetener or, if necessary, one or more flavoring substances, is added.

The dosage of the active ingredients can vary depending on the method of administration, age and weight of the patient, type and severity of the disease to be treated and similar factors. The daily dose is 0.5–1000 mg, preferably 50–200 mg, whereby the dose can be given as a single dose to be administered once or divided into 2 or more daily doses.

The above-described formulations and forms for dispensing are also subjects of this invention.

The production of the compounds according to the invention is carried out according to methods that are known in the art. For example, compounds of general formula I are obtained in that a compound of general formula II

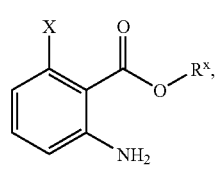

(II)

in which X has the meaning that is indicated in general formula I and $R^x$ stands for hydrogen or $C_1$–$C_6$-alkyl, is first subjected to reductive amination to obtain a compound of general formula (III)

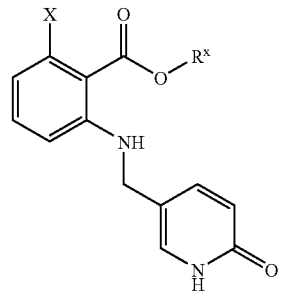

(III)

and then is converted into the corresponding amide of general formula I, and then optionally compounds of general formula I are oxidized to a sulfur compound. The sequence of the steps can also be exchanged, whereby Rx preferably stands for $C_1$–$C_6$-alkyl. If $R^x$ stands for $C_1$–$C_6$-alkyl, it can also optionally first be saponified and then converted into the corresponding amide.

The reductive amination is carried out with aldehydes or ketones, whereby the reaction is performed in the presence of a reducing agent, such as, for example, sodium cyanoborohydride in a suitable inert solvent, such as, for example, ethanol, at temperatures of 0° C. up to the boiling point of the solvent. An addition of acids, such as glacial acetic acid, can also prove advantageous. This reaction sequence can be performed as a single-pot process. It can prove advantageous to isolate the amine that is first produced and then in a separate step to reduce it, for example, with sodium borohydride in solvents such as acetonitrile.

The amide formation is carried out according to methods that are known in the literature.

For amide formation, it is possible to start from a corresponding ester. The ester is reacted according to J. Org. Chem. 1995, 8414 with aluminum trimethyl and the corresponding amine in solvents such as toluene at temperatures of 0° C. to the boiling point of the solvent. If the molecule contains two ester groups, both are converted into the same amide. Instead of aluminum trimethyl, sodium hexamethyldisilazide can also be used.

For amide formation, however, all processes that are known from peptide chemistry are also available. For example, the corresponding acid can be reacted with the amine in aprotic polar solvents, such as, for example, dimethylformamide, via an activated acid derivative that can be obtained, for example, with hydroxybenzotriazole and a carbodiimide, such as, for example, diisopropylcarbodiimide, at temperatures of between 0° C. and the boiling point of the solvent, preferably at 80° C. The reaction between carboxylic acid and amine, however, can also be produced by activation reagents such as HATU (N-dimethylamino-1H-1,2,3-triazolo-[4,5-b]pyridin-1-ylmethylene]-N-methyl-methanaminium hexafluorophosphate-N-oxide), whereby polar aprotic solvents, such as, for example, dimethylformamide, are suitable for the reaction. The addition of a base such as N-methylmorpholine is necessary. The reaction proceeds at temperatures of 0–100° C., whereby the procedure is preferably performed at room temperature. For the amide formation, the process can also be used with the acid halide, the mixed acid anhydride, imidazolide or azide. A previous protection of an additional amino group, for example as an amide, is not necessary in all cases, but can advantageously influence the reaction.

The oxidation of sulfur is carried out according to methods that are known in the literature. The sulfur compound can thus be reacted with oxidizing agents, such as m-chloroperbenzoic acid, in solvents, such as dichloromethane, whereby a mixture of sulfoxide and sulfone can be obtained. Hydrogen peroxide can also be used as an oxidizing agent in solvents, such as, for example, glacial acetic acid. Also, an oxidation with sodium periodate in the presence of ruthenium trichloride, in solvents such as acetonitrile with carbon tetrachloride or sodium periodate in methanol with water, is possible, whereby in the former method, the sulfone is produced and in the latter method, primarily the sulfoxide is produced.

Production of the Compounds According to the Invention

The following examples explain the production of the compounds according to the invention without the scope of the claimed compounds being limited to these examples.

EXAMPLE 1

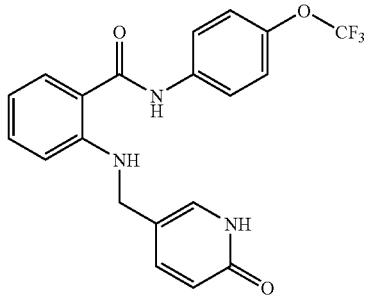

2-[(6-Oxo-1,6-dihydro-pyridin-3-ylmethyl)-amino]-N-(4-trifluoromethoxy-phenyl)-benzamide 441 mg (1.8 mmol) of 2-[(6-oxo-1,6-dihydro-pyridin-3-ylmethyl)-amino]-benzoic acid is introduced into 12 ml of methylene chloride in a moisture-free environment and under argon and mixed in succession with 456 mg (4.5 mmol) of N-methylmorpholine and 336 mg of 4-trifluoromethoxyaniline and 822 mg (2.16 mmol) of HATU (N-dimethylamino-1H-1,2,3-triazolo-[4,5-b]pyridin-1-ylmethylene]-N-methylmethanaminium hexafluorophosphate-N-oxide, and it is stirred for 2.5 hours at room temperature. The acid goes into solution. Then, it is heated for 1.5 hours to a bath temperature of 100° C. First, a product precipitates, which then goes into solution again. It is concentrated by evaporation in a vacuum, and the residue is dispersed into dilute sodium bicarbonate solution and ethyl acetate. The organic phase is washed, dried, filtered and concentrated by evaporation. The residue is chromatographed on 10 g of silica gel (Isolute, flash, SI) with a gradient of $CH_2Cl_2$ on $CH_2Cl_2$:MeOH=9:1 as an eluant, and 414 mg of a product is obtained that is absorptively precipitated with methylene chloride:diisopropyl ether=5:1, and after suctioning off, 364 mg (50.1% of theory) of 2-[(6-oxo-1,6-dihydro-pyridin-3-ylmethyl)-amino]-N-(4-trifluoromethoxy-phenyl)-benzamide with a melting point of 189.2° C. is produced.

Similarly produced are also:

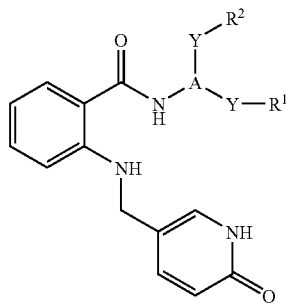

| Example | $Y-R^2$ / A / $Y-R^1$ | Molecular Weight | Melting Point (° C.) or Molar Peak m/e |
|---|---|---|---|
| 1.1 | ⌬—OMe | 349.39 | 150.6 |
| 1.2 | ⌬—OiProp | 377.44 | Resin |
| 1.3 | ⌬—OEt | 363.42 | 172.2 |
| 1.4 | ⌬—OnBu | 405.50 | 159 |
| 1.5 | ⌬—O—CH₂—CF₃ | 417.39 | |
| 1.6 | ⌬—OH | 335.36 | |
| 1.7 | ⌬(m-OCF₃) | 403.36 | |
| 1.8 | ⌬(m-SCF₃) | 419.43 | |
| 1.9 | ⌬(p-SCF₃) | 419.43 | |

-continued

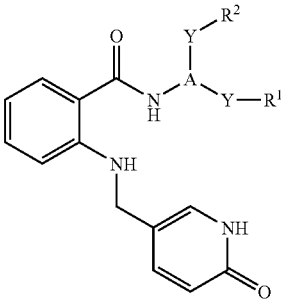

| Example | Y—R¹ / A / Y—R² | Molecular Weight | Melting Point (° C.) or Molar Peak m/e |
|---|---|---|---|
| 1.10 | 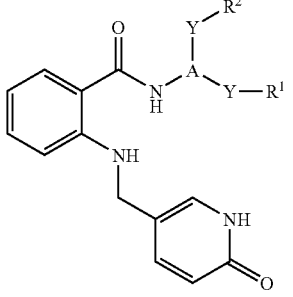 | 393.44 | 111.2 |
| 1.11 | 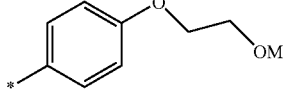 | 417.39 | 191 |
| 1.12 | 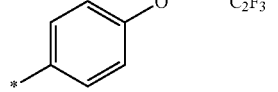 | 385.37 | 178.8 |
| 1.13 | 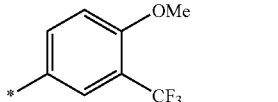 | 379.41 | |
| 1.14 | 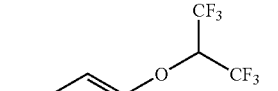 | 385.37 | |
| 1.15 | 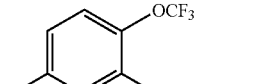 | 385.37 | 110.6 |
| 1.16 | 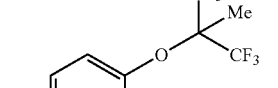 | 349.39 | |
| 1.17 | 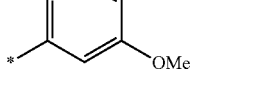 | 377.44 | |
| 1.18 | 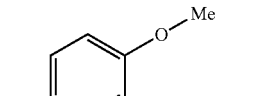 | 431.42 | |

-continued

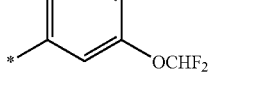

| Example | Y—R¹ / A / Y—R² | Molecular Weight | Melting Point (° C.) or Molar Peak m/e |
|---|---|---|---|
| 1.19 | 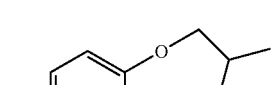 | 467.40 | |
| 1.20 | 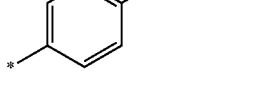 | 485.39 | |
| 1.21 | 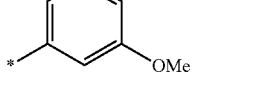 | 513.44 | |
| 1.22 | 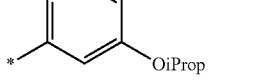 | 383.84 | |
| 1.23 | 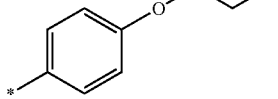 | 391.30 | |

Production of the Starting Materials:

2-[(6-Oxo-1,6-dihydro-pyridin-3-ylmethyl)-amino]-benzoic Acid a.) 2-[(6-Oxo-1,6-dihydro-pyridin-3-ylmethyl)-amino]-benzoic Acid Methyl Ester 4.53 g (30 mmol) of anthranilic acid methyl ester is mixed in 209 ml of methanol with 2.09 ml of glacial acetic acid and 5.76 g (42 mmol) of 2-pyridone5-carbaldehyde, and it is stirred for 24 hours at room temperature under argon and in a moisture-free environment. It is then mixed in portions with 2.64 g (42 mmol) of sodium cyanoborohydride, and it is stirred for 3 days at room temperature. It is then evaporated to the dry state in a vacuum, taken up in 150 ml of dilute sodium bicarbonate solution, absorptively precipitated and suctioned off. As a residue, 4.75 g (61% of theory) of 2-[(6-oxo-1,6-dihydro-pyridin-3-ylmethyl)-amino]-benzoic acid methyl ester is obtained.

b.) 2-[(6-Oxo-1,6-dihydro-pyridin-3-ylmethyl)-amino]-benzoic Acid 3.5 g (12.7 mmol) of 2-[(6-oxo-1,6-dihydro-pyridin-3-ylmethyl)-amino]-benzoic acid-methyl ester is mixed in 15 ml of dimethylformamide with 30 ml of 6N sodium hydroxide solution and stirred for 1.5 hours at room temperature. While being cooled with ice, it is then mixed with about 50 ml of 4N hydrochloric acid, the precipitation is suctioned off, and it is washed with water. 3.1 g, which is taken up in 29.3 ml of 1N sodium hydroxide solution and 142 ml of ethanol, is obtained, and it is heated for 1.5 hours to a bath temperature of 120° C. The ethanol is then drawn off in a vacuum, it is made acidic with 2N hydrochloric acid, and the precipitated product is suctioned off and dried well. 2.9 g (93.5% of theory) of 2-[(6-oxo-1,6-dihydro-pyridin-3-ylmethyl)-amino]-benzoic acid is obtained.

The sample applications below explain the biological action and the use of the compounds according to the invention without the latter being limited to the examples.

Solutions Required for the Tests
Stock Solutions
Stock solution A: 3 mmol of ATP in water, pH 7.0 (−70° C.)
Stock solution B: g-33P-ATP 1 mCi/100 µl
Stock solution C: poly-(Glu4Tyr) 10 mg/ml in water
Solution for Dilutions
Substrate solvent: 10 mmol of DTT, 10 mmol of manganese chloride, 100 mmol of magnesium chloride
Enzyme solution: 120 mmol of tris/HCl, pH 7.5, 10 µM of sodium vanadium oxide Sample Application 1

Inhibition of the KDR- and FLT-1 Kinase Activity in the Presence of the Compounds According to the Invention In a microtiter plate (without protein binding) that tapers to a point, 10 µl of substrate mix (10 µl of volume of ATP stock solution A+25 µCi of g-33P-ATP (about 2.5 µl of stock solution B)+30 µl of poly-(Glu4Tyr) stock solution C+1.21 ml of substrate solvent), 10 µl of inhibitor solution (substances corresponding to the dilutions, 3% DMSO in substrate solvent as a control) and 10 µl of enzyme solution (11.25 µg of enzyme stock solution (KDR, FLT-1 or FLT-4 kinase) are added at 4° C. in 1.25 ml of enzyme solution (dilute). It is thoroughly mixed and incubated for 10 minutes at room temperature. Then, 10 µl of stop solution (250 mmol of EDTA, pH 7.0) is added, mixed, and 10 µl of the solution is transferred to a P 81 phosphocellulose filter. Then, it is washed several times in 0.1 M phosphoric acid. The filter paper is dried, coated with Meltilex, and measured in a microbeta counter.

The IC50 values are determined from the inhibitor concentration, which is necessary to inhibit the phosphate incorporation to 50% of the uninhibited incorporation after removal of the blank reading (EDTA-stopped reaction).

Sample Application 2

Cytochrome P450 Inhibition

The Cytochrome P450 inhibition was performed according to the publication of Crespi et al. (Anal. Biochem., 248, 188–190 (1997)) with use of the baculovirus/insect cell-expressed and human Cytochrome P450 isoenzyme (3A4).

The results of the kinase-inhibition IC50 in nM and the inhibition of the Cytochrome P450 isoenzyme Cyt P 3A4 (IC50, nM) are presented in the table below:

| Example No. | VEGFR II (KDR) [nM] | Inhibition of Cyp 450 3A4 [nM] |
| --- | --- | --- |
| Example 38 from WO 00/27820 | 180 | 4600 |
| Example 5 from WO 03/040102 | 25 | 1500 |
| Example 1.0 | 56 | 5600 |
| Example 1.5 | 59 | 11.000 |

The superior action of the compounds according to the invention compared to the known compounds can be seen clearly from the results.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10327719.6, filed Jun. 13, 2002 and U.S. Provisional Application Ser. No. 60/482,009, filed Jun. 25, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of formula I

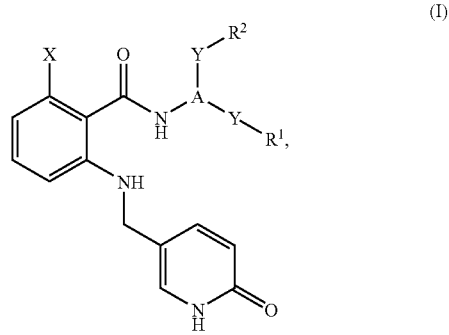

in which
A stands for an aryl or unsubstituted heteroaryl moiety, wherein the heteroaryl is not an indazole group,
X stands for hydrogen or fluorine, R¹ and R², independently of one another, stand for hydrogen, halogen, $C_1$–$C_{12}$-alkyl, $C_1$–$C_{12}$-alkoxy-$C_1$–$C_{10}$-alkylene, $C_3$–$C_{10}$-cycloalkyl or halo-$C_3$–$C_{10}$-cycloalkyl, and Y stands for a bond or for oxygen or for the group —S—, —S(O)— or —SO$_2$—, or a salt thereof.

2. A compound of formula I according to claim 1, in which

A stands for a phenyl or pyridyl,

X stands for hydrogen or fluorine,

R² and R², independently of one another, stand for hydrogen, halogen, $C_1$–$C_{12}$-alkyl, $C_1$–$C_{12}$-alkoxy-$C_1$–$C_{10}$-alkylene, $C_3$–$C_{10}$-cycloalkyl or halo-$C_3$–$C_{10}$-cycloalkyl and Y stands for a bond or for oxygen or for the group —S—, —S(O)— or —SO$_2$—, or a salt thereof.

3. A compound of formula I according to claim 1, in which

A stands for a phenyl,

X stands for hydrogen or fluorine,

R¹ and R², independently of one another, stand for hydrogen, halogen, $C_1$–$C_{12}$-alkyl, $C_1$–$C_{12}$-alkoxy-$C_1$–$C_{10}$-alkylene, $C_3$–$C_{10}$-cycloalkyl or halo-$C_3$–$C_{10}$-cycloalkyl, and Y stands for a bond or for oxygen or for the group —S—, —S(S)— or —SO$_2$—, or a salt thereof.

4. A compound of formula I according to claim 1, in which

A stands for a phenyl,

X stands for hydrogen,

R¹ and R², independently of one another, stand for hydrogen, halogen, $C_1$–$C_{12}$-alkyl, $C_1$–$C_{12}$-alkoxy-$C_1$–$C_{10}$-alkylene, $C_3$–$C_{10}$-cycloalkyl or halo-$C_3$–$C_{10}$-cycloalkyl, and Y stands for a bond or for oxygen or for the group —S—, —S(O)— or —SO$_2$—, or a salt thereof.

5. A pharmaceutical composition comprising a compound according to claim 1 and a pharmaceutically acceptable carrier.

6. A compound according to claim 1, which is an isomer, enantiomer, or diastereomer of said compound.

7. A method for treating Kaposi's sarcoma, leukemia, diabetic retinopathy, neovascular glaucoma, and arteriosclerosis comprising administering to a patient in need thereof an effective amount of a pharmaceutical composition according to claim 5.

8. A compound according to claim 1, wherein at least one of the Y groups is oxygen, —S—, —S(O)— or —SO$_2$—.

9. A compound according to claim 1, wherein at least one of the Y groups is oxygen or —S—.

10. A compound according to claim 1, wherein A stands for: cyclopropenyl, cyclopentadienyl, phenyl, tropyl, cyclooctadienyl, indenyl, naphthyl, azulenyl, biphenyl, fluorenyl, anthracenyl, thienyl, furanyl, pyrrolyl, oxazolyl, thiazolyl, imidazolyl, pyrazolyl, isoxazolyl, isothiazolyl, oxadiazolyl, triazolyl, thiadiazolyl, benzofuranyl, benzothienyl, benzoxazolyl, benzimidazolyl, indolyl, isoindolyl, pyridyl, pyridazinyl, pyrimidinyl, pyrazinyl, triazinyl, quinolyl, isoquinolyl, azocinyl, indolizinyl, purinyl, quinolinyl, isoquinolinyl, cinnolinyl, phthalazinyl, quinazolinyl, quinoxaliriyl, naphthyridinyl, pteridinyl, carbazolyl, acridinyl, phenazinyl, phenothiazinyl, phenoxazinyl, xanthenyl, or oxepinyl.

11. A compound according to claim 1, which is

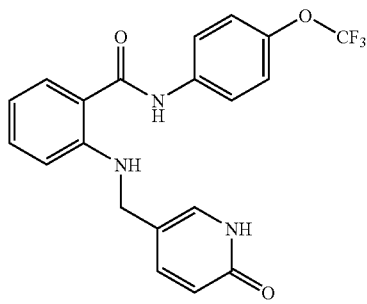

or

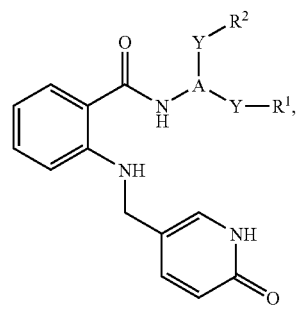

wherein

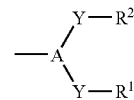

is

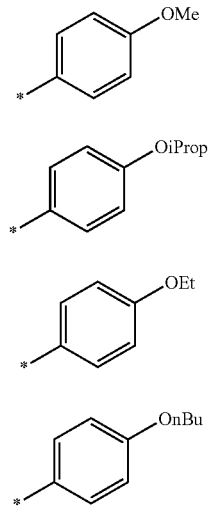

-continued
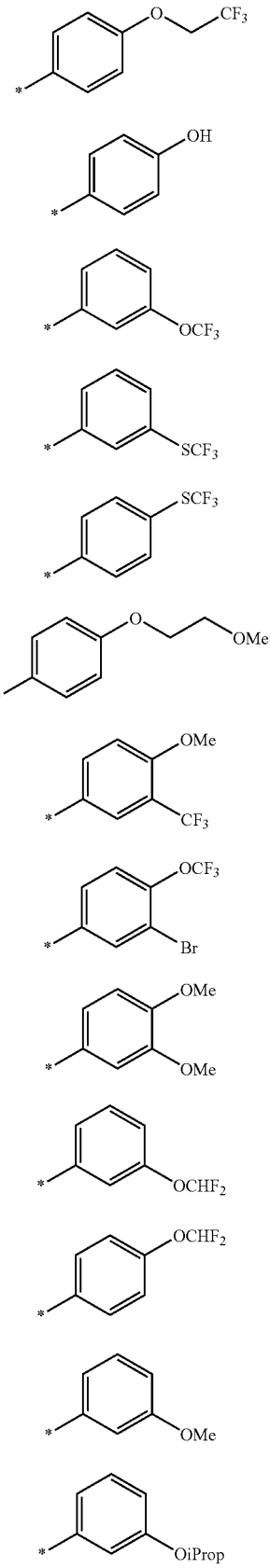
-continued
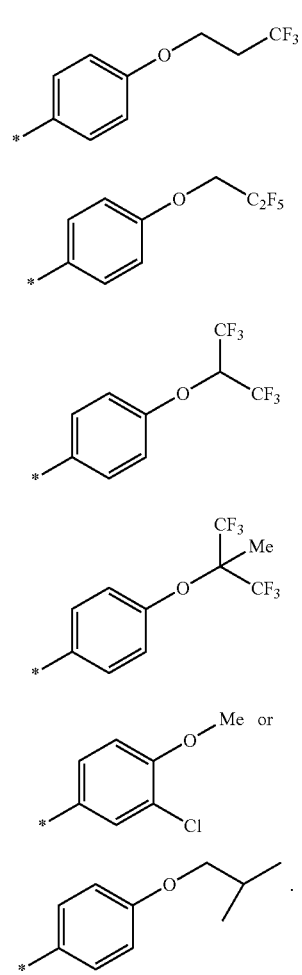
12. A compound according to claim 1, which is
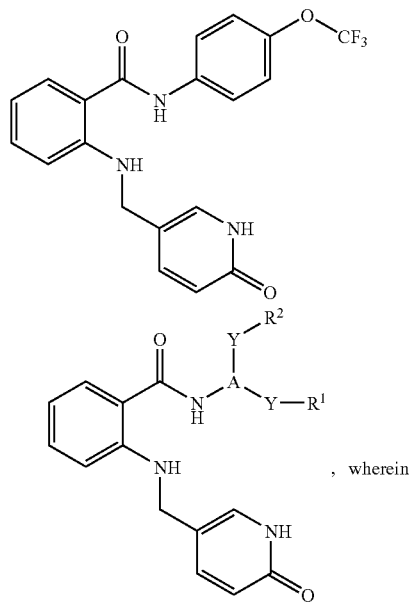
, wherein -continued
—A⟨Y—R²/Y—R¹  is  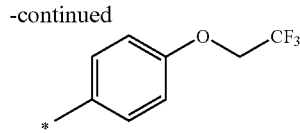.
13. A compound according to claim 1, wherein R¹ or R² is —OCF₃, —OMe, —OiProp, —OEt, —OnBu, —OCH₂CF₃, —OH, —SCF₃, —OCH₂CH₂OMe, —OCHF₂, —OCH₂CH₂CF₃, —OCH₂CF₂CF₃, —OCH(CF₃)₂, —OCH(CF₃)₂CH₃, —Cl, or —OCH₂CH(CH₃)₂.
14. A pharmaceutical composition comprising a compound according to claim 11 and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 7,202,260 B2 | Page 1 of 1 |
| APPLICATION NO. | : 10/866078 | |
| DATED | : April 10, 2007 | |
| INVENTOR(S) | : Andreas Huth et al. | |

It is certified that error appears in the above-identified patent and that said Letters Patent is hereby corrected as shown below:

Column 13, line 12, reads "$R^2$ and $R^2$" should read -- $R^1$ and $R^2$ --

Column 13, line 28, reads "–S(S)—" should read -- –S(O)— --

Signed and Sealed this

Twenty-third Day of October, 2007

JON W. DUDAS
*Director of the United States Patent and Trademark Office*